United States Patent [19]
Huang

[11] Patent Number: 4,792,560
[45] Date of Patent: Dec. 20, 1988

[54] QUINOLINE HYDROXAMATES AND THEIR USE AS MODULATORS OF ARACHIDONIC ACID METABOLIC PATHWAYS

[75] Inventor: Fu-chih Huang, Leonia, N.J.

[73] Assignee: Rorer Pharmaceutical Corporation, Fort Washington, Pa.

[21] Appl. No.: 830,798

[22] Filed: Feb. 19, 1986

Related U.S. Application Data

[63] Continuation-in-part of Ser. No. 719,199, Apr. 3, 1985, abandoned.

[51] Int. Cl.$^4$ .................... A61K 31/47; C07D 215/14
[52] U.S. Cl. .................................... 514/311; 546/175
[58] Field of Search ...................... 546/175; 514/311

[56] References Cited

U.S. PATENT DOCUMENTS

3,481,970  12/1969  Levy ........................... 260/500.5 H

FOREIGN PATENT DOCUMENTS

1102867  2/1968  United Kingdom ................ 514/575

*Primary Examiner*—Glennon H. Hollrah
*Assistant Examiner*—D. B. Springer

[57] ABSTRACT

This invention relates to new chemical compounds possessing valuable pharmaceutical activity, particularly as lipoxygenase inhibitors possessing anti-inflammatory and anti-allergic properties.

12 Claims, No Drawings

QUINOLINE HYDROXAMATES AND THEIR USE AS MODULATORS OF ARACHIDONIC ACID METABOLIC PATHWAYS

This is a continuation-in-part of U.S. patent application Ser. No. 719,199, which was filed on Apr. 3, 1985, now abandoned.

This invention relates to new chemical compounds possessing valuable pharmaceutical activity, particularly as lipoxygenase inhibitors possessing anti-inflammatory and anti-allergic properties.

The present new compounds are of the formula:

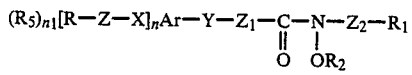

and salts thereof; wherein
- $R_2$ is H, lower alkyl, formyl or $C_2$-$C_{10}$ alkanoyl;
- R and $R_1$ are each independently hydrogen, lower cycloalkyl, fused cycloalkyl or lower alkyl-substituted fused cycloalkyl, lower alkyl, phenyl, naphthyl or a nitrogen, oxygen, or sulfur heterocyclic ring or heterocyclic-lower alkyl;
- Z, $Z_1$ and $Z_2$ are each a chemical bond, or an alkylene chain or a mono- or di-substitued lower cycloalkyl or heterocyclic lower alkyl, and the substituents are hydrogen, lower alkyl, aryl, lower aralkyl, lower alkoxy, hydroxy, lower aralkoxy, carboxy, lower carbalkoxy, carbaryloxy, lower carbaralkoxy, amino, lower alkyl amino, amino loweralkyl, di-loweralkylamino or cyano;
- X and Y are each independently O, S, $CR_3R_4$ or a chemical bond;
- $R_3$ and $R_4$ are each independently H or lower alkyl;
- Ar is phenyl or naphthyl or a nitrogen, oxygen, or sulfur heterocyclic;
- $R_1$ and $R_2$ together may form an alkylene bridge of the formula $R_2$-M-$R_1$ wherein M is O, $NR_3$, S, or $CH_2$;
- each $R_5$ is hydrogen, aryl, lower alkanoyl, formyl, nitro, cyano, amino, lower aminoalkyl, lower alkylamino, lower aralkylamino, halo, trihaloalkyl, carbamoyl or aroyl;
- n is an integer from 0-2; and
- n' is an integer from 1-2.

The heterocyclic rings exemplary of Ar, R, $R_1$, Z, $Z_1$, and $Z_2$ are 5-10 membered rings containing at least one oxygen, sulfur, or nitrogen and include the so-called benzoheterocyclic rings. Exemplary heterocyclics include furan, thiophene, pyrrole, piperidine, dihydrofuran, pyridine, thiazole, piperazine, oxazole, benzofuran, tetrahydroquinoline, quinoline, indole, dihydroindole, benzothiophene, dihydrobenzothiophene, benzoxazole, and similar heterocyclic rings. The preferred heterocyclic rings are quinoline and pyridine.

The heterocyclic-lower alkyl and the aryl cycloalkyl lower alkyl groups include naphthylmethyl, pyridylethyl, indolylethyl, quinolinylmethyl, pyrrolylmethyl, indanylmethyl, indanylethyl and the like.

The non-heterocyclic aryl moieties of R and $R_1$ include phenyl, or α- or β-naphthyl, etc.

The cycloalkyl and fused cycloalkyl groups may be mono or polycyclic and contain from 3 to 20 carbons. These groups include cyclopropyl, cyclopentyl, cyclohexyl, cycloheptyl, bornyl, norbornyl, indanyl and the like. These groups may be partially unsaturated and carry substituents such as halogen, hydroxy, lower alkyl, lower alkoxy, amino, lower alkylamino, di (lower alkyl) amino, thiol, lower alkylmercapto, nitro, trifluoromethyl, lower aralkyl, aryloxy, lower aralkoxy, and the like.

Exemplary alkanoyl groups include acetyl, propionyl, butyryl, valeryl, isobutyryl, pivaloyl, neopentylcarbonyl, octanoyl, and decanoyl.

The alkyl groups, either alone or within the various substituents defined hereinbefore are preferably lower alkyl which may be straight or branched chain and include methyl, ethyl, propyl, isopropyl, butyl, isobutyl, amyl, hexyl and the like.

The halo atoms in halo and trihalomethyl are Cl, Br, I and F.

The alkylene chain representative of Z, $Z_1$ and $Z_2$ can be branched or straight chain containing up to 6 carbon atoms in the principal chain and up to a total of 10 carbon atoms. It is preferred that Z, $Z_1$ and $Z_2$ are independently a chemical bond or an alkylene chain containing up to 5 carbon atoms in the principal chain. It is especially preferred that Z and $Z_1$ are independently a chemical bond or an alkylene chain containing up to 3 carbon atoms in the principal chain and that $Z_2$ is an alkylene chain containing up to 5 carbon atoms in the principal chain.

The preferred R and $R_1$ are independently hydrogen, lower alkyl, phenyl, naphthyl or quinolyl. Whenever R and $R_1$ are other than hydrogen, they each may carry substituents such as hydrogen, lower alkyl, aryl, lower aralkyl, hydroxy, lower alkoxy, lower aralkoxy, aryloxy, cyano, carboxy, halogen, amino, lower alkylamino, dilower alkyl amino, mercapto, lower alkylthio, carboxy, lower carbalkoxy, carbaryloxy, lower carbaralkoxy, nitro, lower alkanoyl, formyl, trihalomethyl, and the like. It is preferred that R and $R_1$ be substituted with halo, hydroxy, lower alkyl, lower alkoxy, amino, cyano, lower alkylamino, lower aralkyl, aryloxy, lower aralkoxy, nitro or trihalomethyl.

The preferred X and Y are oxygen and $CR_3R_4$ wherein $R_3$ and $R_4$ are as defined hereinabove. Especially preferred X is oxygen and especially preferred Y is $CR_3R_4$. It is preferred that $R_4$ is hydrogen.

The preferred compounds of the present invention are those in which n is 0 or 1 and $n_1$ is 1. In addition, it is preferred that $R_2$ is hydrogen or lower alkyl, especially hydrogen.

Compounds which are particularly preferred are those in which Ar is phenyl or naphthyl and most preferred are those in which Ar is phenyl. It is preferred that Ar is substituted with hydrogen, hydroxy, alkoxy, halo, amino, cyano, trihaloalkyl, or alkyl.

Additional variations in the structural formula representing the instant compounds can be effected without significantly altering the therapeutic properties, e.g., lipoxygenase inhibition. For example, the aryl groups and the heterocyclic groups can be substituted by one or more of a variety of substituents such as alkyl, aryl, halogen, hydroxy, alkoxy, aryloxy, such as phenoxy, benzyloxy, carboxy, carbalkoxy, carbamoyl, nitrilo, amino, alkylamino, dialkylamino, formyl, trihalomethyl, and nitro groups.

The compounds of the present invention may contain one or more asymmetric carbon atoms and may exist in racemic and optically active forms. All of these compounds are contemplated to be within the scope of the present invention.

The present compounds can be prepared by art-recognized procedures from known compounds or readily preparable intermediates. Useful intermediates of the present invention are hydroxamates of formula II:

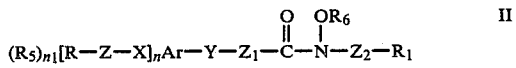

wherein R, $R_1$, $R_5$, Z, $Z_1$, $Z_2$, X, Y, n, $n_1$ and Ar are as defined above, and $R_6$ is a protecting group, e.g., alkyl, aryl or aralkyl. Compounds of Formula II are easily converted to compounds of Formula I wherein $R_2$ is hydrogen, by removal of $R_6$, a protecting group, in the presence of an acid, such as HI, HBr and the like or Lewis Acids, such as $BF_3$, $BCl_3$, $AlCl_3$ and the like. Such protecting groups are well known in the art and commonly include tertiary alkyl groups, such as tertiary, butyl, tert-amyl groups and the like and aralkyls, such as benzyl. Other removable groups include sulfonates; borate esters; nitrate esters; alkoxyalkylethers, such as benzyloxymethylether, t-butoxymethyl ether, ethoxyethyl ethers, and the like; silyl ethers, such as 2-(Trimethylsilyl)ethoxymethyl ethers, tri-methylsilyl ethers; tetrahydropyranyl ethers; tetrahydrothiofuranyl ethers; t-butyl ethers; benzyl ethers, esters, such as formates and benzoates, and carbonates, such as alkylethyl carbonates, and alkyl benzyl carbonates. Such groups are removable by art recognized procedures, e.g., acid hydrolysis for tertiary butyl groups, t-butoxymethyl ether, tetrahydropyranyl ethers, t-butylethers, benzyl ethers, borates, and sulfonates; mild basic hydrolysis, for silyl ethers, formate esters, and benzoates; and catalytic hydrogenation, e.g., using Pd/C, for removal of benzyl groups and alkyl benzyl carbonates. As in any organic reaction, solvents can be employed, such as methylene chloride, diethyl ether, tetrahydrofuran, dioxane, chloroform, and the like. The reaction is normally effected at or near room temperature, although temperatures from 0° C. up to the reflux temperature of the mixture can be employed. The compounds of Formula II wherein $OR_2$ is hydroxy can be converted to other groups by conversion and substitution reactions known in the art. For example, compounds wherein $R_2$ is alkoxy can be prepared from the corresponding OH via Williamson synthesis or by the reaction with the appropriate alkene.

Compounds of Formula I wherein $R_2$ is H or lower alkyl can also be prepared by the direct condensation of the reaction or carboxylic acids of Formula III with hydroxyl amine derivatives of Formula IV:

III

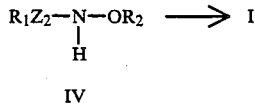

IV

By conversion or substitution reactions, compounds of Formula I can be converted to other compounds within the scope of Formula I. For example, compounds of Formula I in which $R_2$ is alkanoyl can be prepared from those compounds of Formula I wherein $R_2$ is hydrogen by acylation with an alkanoic acid acylating derivative. Formula I compounds wherein $R_2$ is hydrogen can be formylated by standard procedures of formylation known in the art to produce Formula I compounds wherein $R_2$ is formyl.

Compounds of formula II can be formed from the reaction of carboxylic acids of formula III with hydroxylamine derivatives of formula V under amide forming conditions:

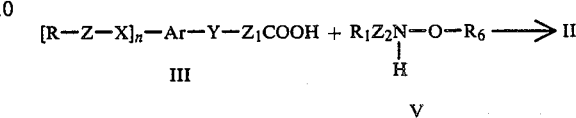

The amide forming conditions referred to herein involve the use of known derivatives of the described acids, such as the acyl halides, anhydrides, mixed anhydrides, lower alkyl esters, carbodiimides, carbonyldiimidazoles, and the like. The reactions are carried in organic solvents such as acetonitrile, tetrahydrofuran, dioxane, acetic acid, methylene chloride, ethylene chloride and similar such solvents. The amide forming reaction will occur at room temperature or at elevated temperatures. The use of elevated temperature is for convenience in that it permits somewhat shortened reaction periods. Temperatures ranging from 0° C. up to the reflux temperature of the reaction system can be employed. As a further convenience, the amide-forming reaction can be effected in the presence of a base, such as tertiary organic amines, e.g., trimethylamine, pyridine, picolines and the like, particularly where hydrogen halide is formed by the amide-forming reaction, e.g., acyl halide and hydroxylamine. Of course, in those reactions where hydrogen halide is produced any of the commonly used hydrogen halide acceptors can also be used.

Compounds of formula V are prepared from the corresponding hydroxylamines. $R_6$ is a protecting group which minimizes any possible side reaction and formation of O-acylhydroxylamines from the reaction of the carboxyl group of the carboxylic acid (III) with the hydroxy moiety of a free hydroxylamine.

Various substituents on the present new compounds, e.g., as defined in Ar, R, $R_1$, Z, $Z_1$, and $Z_2$, can be present in the starting compounds, added to any one of the intermediates or added after formation of the hydroxamate products by the known methods of substitution or conversion reactions. If the substituents themselves are reactive, then the substituents can themselves be protected according to the techniques known in the art. A variety of protecting groups known in the art may be employed. Examples of many of these possible groups may be found in "Protective Groups in Organic Synthesis" by T. W. Green, John Wiley and Sons, 1981. For example, the nitro groups can be added to the aromatic ring by nitration and the nitro group converted to other groups, such as amino by reduction, and halo by diazotization of the amino group and replacement of the diazo group. Alkanoyl groups can be substituted onto the the aryl groups by Friedel-Crafts acylation. The acyl groups can then be transformed to the corresponding alkyl groups by various methods, including the Wolff-Kishner reduction and Clemmenson reduction. Amino groups can be alkylated to form mono and dialkylamino groups; and mercapto and hydroxy groups can be alkylated to form corresponding ethers. Primary alcohols can be oxidized by oxidizing agents known in the art to form carboxylic acids or aldehydes, and secondary alcohols can be oxidized to form ketones. Thus, substitution or alteration reactions can be employed to provide a variety of substituents throughout the molecule of the starting material, intermediates, or the final product.

The present new compounds form salts with acids when a basic amino function is present and salts with bases when an acid function, i.e., carboxyl, is present. All such salts are useful in the isolation and/or purification of the new products. Of particular value are the pharmaceutically acceptable salts with both acids and bases. Suitable acids include, for example, hydrochloric, sulfuric, nitric, benzenesulfuric, toluenesulfonic, acetic, malic, tartaric and the like which are pharmaceutically acceptable. Basic salts for pharmaceutical use are the Na, K, Ca and Mg salts.

The compounds of the present invention can be administered to the host in a variety of forms adapted to the chosen route of administration, i.e., orally, intraveneously, intramuscularly or subcutaneous, topically or inhalation routes.

The active compound may be orally administered, for example, with an inert diluent or with an assimilable edible carrier, or it may be enclosed in hard or soft shell gelatin capsules, or it may be compressed into tablets, or it may be incorporated directly with the food of the diet. For oral therapeutic administration, the active compound may be incorporated with excipients and used in the form of ingestible tablets, buccal tablets, troches, capsules, elixirs, suspensions, syrups, wafers, and the like. Such compositions and preparations should contain at least 0.1% of active compound. The percentage of the compositions and preparations may, of course, be varied and may conveniently be between about 2 to about 60% of the weight of the unit. The amount of active compound in such therapeutically useful compositions is such that a suitable dosage will be obtained. Preferred compositions or preparations according to the present invention are prepared so that an oral dosage unit form contains between about 50 and 300 mg of active compound.

The tablets, troches, pills, capsules and like may also contain the following: a binder such as gum tragacanth, acacia, corn starch or gelatin; excipients such as dicalcium phosphate; a disintegrating agent such as corn starch, potato starch, alginic acid and the like; a lubricant such as magnesium stearate; and a sweetening agent such as sucrose, lactose or saccharin may be added or a flavoring agent such as peppermint, oil of wintergreen, or cherry flavoring. When the dosage unit form is a capsule, it may contain, in addition to materials of the above type, a liquid carrier. Various other materials may be present as coatings or to otherwise modify the physical form of the dosage unit. For instance, tablets, pills, or capsules may be coated with shellac, sugar or both. A syrup or elixir may contain the active compound, sucrose as a sweetening agent, methyl such as cherry or orange flavor. Of course, any material used in preparing any dosage unit form should be pharmaceutically pure and substantially non-toxic in the amounts employed. In addition, the active compound may be incorporated into sustained-release preparations and formulations.

The active compound may also be administered parenterally or intraperitoneally. Solutions of the active compound as a free base or pharmacologically acceptable salt can be prepared in water suitably mixed with a surfactant such as hydroxypropylcellulose. Dispersions can also be prepared in glycerol, liquid polyethylene glycols, and mixtures thereof and in oils. Under ordinary conditions of storage and use, these preparation contain a preservative to prevent the growth of microorganisms.

The pharmaceutical forms suitable for injectable use include sterile aqueous solutions or dispersions and sterile powders for the extemporaneous preparation of sterile injectable solutions or dispersions. In all cases the form must be sterile and must be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, liquid polyethylene glycol, and the like), suitable mixtures thereof, and vegetable oils. The proper fluidity can be maintained, for example, by the use of a coating such as lecithin, by the maintenance of the required particle size in the case of dispersion and by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

Sterile injectable solutions are prepared by incorporating the active compound in the required amount in the appropriate solvent with various of the other ingredients enumerated above, as required, followed by filtered sterilization. Generally, dispersions are prepared by incorporating the various sterilized active ingredient into a sterile vehicle which contains the basic dispersion medium and the required other ingredients from those enumerated above. In the case of sterile powders for the preparation of sterile injectable solutions, the preferred methods of preparation are vacuum drying and the freeze-drying technique which yield a powder of the active ingredient plus any additional desired ingredient from previously sterile-filtered solution thereof.

The following examples further illustrate the invention.

EXAMPLE 1

α-(4-Benzyloxyphenyl)-N-benzyl acetohydroxamate

A. N,O-Dibenzylhydroxylamine

A mixture of 4 g of O-benzylhydroxylamine, 4.28 g of benzyl bromide, and 12 g of $K_2CO_3$ in 50 ml of ethanol was stirred at 50° C. overnight. After removal of organic solvent, water was added to the residue and the mixture was then extracted with ethyl acetate. The combined extracts were dried and evaporated to give 4 g of crude product. Purification by dry column chromatography gave 1.8 g of oily product.

B. α-(4-Benzyloxyphenyl)-N,O-dibenzyl acetohydroxamate

A mixture of 4-benzyloxyphenyl acetic acid (1.2 g) and 0.9 g of 1,1'-carbonyldiimidazole in 20 ml of $CH_2Cl_2$ was stirred at 50° C. for 1 hour. Then 1.1 g of N,O-dibenzylhydroxylamine was added and the reaction was kept at 50° C. overnight. After evaporation of solvent, the residue was extracted with ether. The ethereal solution was washed with water, 1N HCl, dried and evaporated to dryness. Purification by dry column chromatography gave 1.2 g of oily product.

C. α-(4-Benzyloxyphenyl)-N-benzyl acetohydroxamate

To a methylene chloride solution of the product from B (1.2 g in 30 ml) at −80° C. was added dropwise 4 ml (1M) of boron trichloride solution in $CH_2Cl_2$. The reaction mixture was warmed and kept at room temperature for 3 hours. Solvent was evaporated and methanol was added to the residue and evaporated to dryness again. The crude product thus obtained was purified by dry column chromatographic method to give 500 mg of solid, which was washed with ether-hexane solution to give 350 mg of product as a white solid: mp 142°–143° C.

EXAMPLE 2

α-(4-Benzyloxyphenyl)-N-phenethyl acetohydroxamate

A. Phenylacetaldehyde O-benzyloxime

A mixture of 5 g of phenylacetaldehyde, 6.7 g of O-benzylhydroxylamine hydrochloride, and 3 g of potassium carbonate in 30 ml of aqueous methanol (1:1) was refluxed for 2 hours. The aqueous solution was extracted with ethyl acetate and the organic solution was dried and evaporated to give 8 g of crude product which was used without purification.

B. O-Benzyl-N-phenethylhydroxylamine

To a methanolic solution of the crude product from 2A (8 g in 50 ml) was added portionwise 5 g of $NaCNBH_3$ over a period of 1 hour. The reaction solution was maintained at pH 3 by occasional addition of 1N $HCl/CH_3OH$ solution using bromocresol green as an indicator. The reaction mixture was then stirred for an additional 1 hour. The solution was made basic to pH 10 and then extracted with ethyl acetate. The combined organic extracts were dried, evaporated to dryness and the residue was purified by dry column chromatography to give 5.5 g of oily product.

C. α-(4-Benzyloxyphenyl)-N-phenethyl acetohydroxamate

The compound was prepared in an identical manner as described in 1B and 1C. A solid was isolated; m.p. 114°–115° C.

EXAMPLE 3

α-methyl-α-(4-(2-methylpropyl)phenyl)-N-benzyl acetohydroxamate

The reaction of N, O-dibenzylhydroxylamine and α-methyl-4-(2-methylpropyl)phenylacetic acid according to the procedure described in Example 1B and 1C afforded the product; m.p. 96°–97° C.

EXAMPLE 4

α-Methyl-α-[2-(6-methoxynaphthyl)]-N-benzyl acetohydroxamate

This compound was prepared in an identical manner as described in Example 1B and 1C, except 2-(6-methoxy-2-naphthyl)propionic acid was substituted for 4-benzyloxyphenyl acetic acid; m.p. 162°–163° C.

EXAMPLE 5

α-(4-(2-methylpropyl)phenyl)-α-methyl-N-(2-phenethyl)acetohydroxamate

The reaction of α-methyl-4-(2-methylpropyl)-phenylacetic acid with O-benzyl-N-phenethylhydroxylamine, according to the procedure of Example 2C, afforded an oil.

EXAMPLE 6

α-4-Benzyloxyphenyl-N-(3-phenylpropyl)acetohydroxamate

This solid was prepared by reacting 4-benzyloxyphenylacetic acid with O-benzyl-N-phenylpropylhydroxylamine according to the procedure of Examples 1B and 1C; m.p. 130°–131° C.

EXAMPLE 7

α-(4-Hydroxyphenyl)-N-(α-methylbenzyl)acetohydroxamate

The product was prepared by reacting 4-hydroxyphenylacetic acid with O-benzyl-N-α-methylbenzylhydroxylamine according to the procedure of Examples 1B and 1C; m.p. 144°–146° C.

EXAMPLE 8

α-(4-(2-Methylpropyl)phenyl)-α-methyl-N-(α-methylbenzyl)acetohydroxamate

The solid was prepared by reacting 2-methyl-2-[4-(2-methylpropyl)]phenylacetic acid with O-benzyl-N-(α-methylbenzyl)hydroxylamine according to the procedure of Examples 1B and 1C. Two sets of diastereoisomers were isolated. The diastereoisomers were separated using column chromatography. Racemic mixture of the (R,R) and (S,S) enantiomers and the (R,S) and (S,R) enantiomers were isolated.
m.p. of (R,R)—(S,S) mixture: 93°–94° C.
m.p. of (R,S)—(S,R) mixture: 123°–124° C.

EXAMPLE 9

α-phenethyl-N-phenethylacetohydroxamate

This solid was prepared by reacting 4-phenylbutanoic acid with O-benzyl-N-phenethylhydroxylamine according to the procedure of Examples 1B and 1C; m.p. 56°–58° C.

EXAMPLE 10

α-(4-Benzyloxyphenyl)-N-(α-methylbenzyl)acetohydroxamate

The product was prepared by reacting 4-benzyloxyphenylacetic acid with O-benzyl-N-α-methylbenzylhydroxylamine according to the procedure of Example 1B and 1C; m.p. 140°–141° C.

EXAMPLE 11

α-(4-Benzyloxyphenyl)-N-(1-benzylpropyl)acetohydroxamate

The product was prepared by reacting 4-Benzyloxyphenyl acetic acid with O-benzyl-N-1-(benzylpropyl)-hydroxylamine according to the procedure of Examples 1B and 1C; m.p. 100°–101° C.

EXAMPLE 12

α-(4-Benzyloxyphenyl)-N-methyl acetohydroxamate

A mixture of 4-benzyloxyphenyl acetic acid (1.6 g) and 1.1 g of 1,1-carbonyldiimidazole in 15 mL of $CH_2Cl_2$ was stirred at 50° C. for 1 h. Then a solution of 0.55 g of N-methylhydroxylamine.HCl and 0.7 g of triethylamine in 10 mL of $CH_2Cl_2$ was added and the reaction mixture was stirred at 50° C. for two days. The organic solution was washed with $H_2O$, dried, and evaporated to dryness. Purification by dry column chromatagraphy gave 0.1 g of white solid product; m.p. 94°–96° C.

EXAMPLE 13

In a similar fashion according to the procedures of the preceding examples and using the appropriate starting materials, the following compounds were prepared:

N-Hydroxy-N-Methyl-(3-((quinolin-2-yl)methoxy)-phenylacetamide (m.p. 69°–70° C.);
N-Hydroxy-N-Methyl-5-phenylvaleramide (liquid);
N-Hydroxy-N-Methyl-4-((quinolin-2-yl)methoxy)-phenylacetamide (m.p. 144° C.);
N-Hydroxy-N-Methyl-4-(4-methoxyphenyl)butyramide (m.p. 74°–75° C.);
N-Hydroxy-N-(2-phenylethyl)-2-(3-benzyloxyphenyl)-propionamide (liquid);
N-(3-carboxypropyl)-N-hydroxy-4-phenylbutyramide (liquid);
N-(2-phenethyl)-N-hydroxy-5-phenylvaleramide (m.p. 79°–80° C.);
N-Hydroxy-N-(2-Methyl-2-(4-methoxyphenyl)ethyl)4-hydroxyphenylacetamide (m.p. 143°–146° C.);
N-Hydroxy-N-(2-phenylethyl)-2-(3-benzoylphenyl)-propionamide (liquid);
N-Hydroxy-N-(4-chlorophenethyl)-4-Benzyloxy phenylacetamide (m.p. 115°–116° C.);
N-(3-carboxypropyl)-N-hydroxy-4-phenylbutyramide (m.p. 63°–64° C.);
N-Benzyl-N-hydroxy-4-phenylbutyramide (m.p. 71°–72° C.);
N-Hydroxy-N-(2-phenethyl)-2-phenoxyacetamide (m.p. 155°–156° C.);
N-Hydroxy-N-(2-methyl-2-(4-benzyloxyphenyl)ethyl)-4-benzyloxyphenylacetamide (m.p. 131°–134° C.);
N-Hydroxy-N-(1-benzylpropyl)-4-phenylbutyramide (m.p. 71°–72° C.);
N-Hydroxy-N-(3-phenylpropyl)-3-phenylpropionamide (m.p. 66°–67° C.);
N-Hydroxy-N-(2-phenethyl)-3-phenoxypropionamide (m.p. 79°–80° C.);
N-Hydroxy-N-2-phenethyl)-4-(4-methoxyphenyl)-butyramide (m.p. 81°–82° C.);
N-Hydroxy-N-(2-phenethyl)-2-(4-chlorobenzyloxyphenyl)acetamide (m.p. 146°–150° C.);
N-Hydroxy-N-propyl-2-(4-benzyloxyphenyl)acetamide (m.p. 93°–94° C.);
N-Hydroxy-N-methyl-2-(3-chloro-4-benzyloxyphenyl)acetamide (m.p. 109°–111° C.);
N-Hydroxy-N-(2-phenethyl)-4-methoxyphenylacetamide (m.p. 87°–88° C.); and
N-(t-Butyl)-N-Hydroxy-4-benzyloxyphenylacetamide (m.p. 128°–130° C.).

In a similar fashion according to the procedures of the preceding examples, the following compounds can be prepared from appropriate starting materials:

α-(3-(2-quinolinylmethoxy)phenyl)-N-(2-phenethyl)acetohydroxamate;
α-(5-benzyloxy-2-pyridyl)-N-benzylacetohydroxamate;
α-(4-phenoxyphenyl)-N-pentylacetohydroxamate;
α-(4-benzyloxyphenyl)-N-(5-pentanoic acid)acetohydroxamate;
α-(4-benzyloxybenzyl)-N-(2-phenethyl)acetohydroxamate;
α-(4-benzyloxy-3-chlorophenyl)-N-(2-phenethyl)acetohydroxamate;
α-(4-benzyloxy-3-chlorophenyl)-N-(1-carbethoxy-2-phenylethyl)acetohydroxamate;
α-(3-benzyloxyphenyl)-N-(1-methyl-2-phenethyl)acetohydroxamate;
α-(2-pyridyl)-N-phenethyl acetohydroxamate;
α-(4-benzyloxyphenyl)-N-(2-pyridylmethyl)acetohydroxamate;
α-(4-benzyloxyphenyl)-N-phenethyl-O-acetyl acetohydroxamate N-hydroxy-N-phenethyl-4-benzyloxybenzamide.

The compounds of the present invention have potent activity in regulating lipoxygenase and, as such, possess therapeutic value in the treatment of inflammatory conditions and allergic responses such as anaphlaxis and asthma.

Lipoxygenases in mammals have been found in the lung, platelets, and white cells. They are enzymes capable of oxidizing arachidonic acid into hydroperoxyeicosatetraenoic acids (HPETE's) and their stable products hydroxyeicosatetraenoic acids (HETEs). Lipoxygenases are classified according to the position in the arachidonic acid which is oxygenated. Platelets metabolize arachidonic acid to 12-HETE, while polymorphonuclear (PMN) leukocytes contain 5 and 15 lipoxygenases. It is known that 12-HETE and 5,12-diHETE are chemotactic for human nuetrophils and eosinophils, and may augment the inflammation process. 5-HETE is known to be a precursor of slow reacting substance anaphylaxis (SRS-A). The SRS family of molecules, such as leukotrienes B, C, and D, have been shown to be potent bronchoconstrictors (see, NATURE 288, 484–486 (1980).

The following protocols describe assays that detect inhibitors of the lipoxygenase. Such inhibitors are believed to be capable of modulating the biosynthesis of the leukotrienes, a property believed to be useful in treating asthma and inflammatory disease states.

Biosynthesis of 12-HETE by Intact Platelets (12-LOX)

Four to five sprague-Dawley rats (200–300 g) are individually anesthetized with diethylether in a large glass desiccator placed in a hood. A 100 ml beaker packed with cotton which is saturated with ether is placed over the rat's head to prevent the animal from regaining consciousness during the isolation procedure. A twenty ml syringe containing 1.0 ml of 3.8% sodium citrate is used to draw 9 mls of blood from the abdominal aorta. The blood/citrate is then gently mixed and transferred to a 15 ml polypropylene centrifuge tube, which is capped and kept at RT.

Platelet Rich Plasma (PRP) is prepared by centrifugation (in a Damon table top centrifuge) of the citrated blood at 200 g for 10 min at room temperature. Platelets are collected by centrifugation of the PRP at 1000 g for 10 min at RT. Platelet suspension is prepared by suspending the platelet pellet in 2 ml of PBS (without $Ca^{2+}$ or $Mg^{2+}$) for each rat used. An aliquot of 200 ul of the rat platelet suspension thus obtained is incubated with 24 ul of test compound or solvent (DMSO; final concentration of 0.1%) for 5 min at 30°. The total assay volume is 244 ul. The reaction is initiated by the addition of 20 ul of a calcium/($^{14}$C)-AA solution (final concentration of 1.42 mM and 4 uM, respectively). After 3 min at 30°, the reaction is quenched by the addition of 15 ul of citric acid (1M) and NDGA (5 mM). Unlabled 15-HETE and ($^3$H)-12-HETE are added to the citric acid-quenched samples as internal standards. After chromatography of the extracted products on silica gel, ($^{14}$C)-12-HETE is located by the UV absorbence of the added 15-HETE (with which it cochromatographs) and is quantitated by scintillation spectroscopy.

Protocol for Detecting Inhibitors of the Lipoxygenase Pathway

A suspension of rat neutrophils in buffer is incubated for 3 minutes at 30° C. with [$^{14}$C]-arachidonic acid (AA) and Calcium Ionophore A23187. Citric acid (2M) is used to quench the reaction. Following the addition of a trace amount of ($^3$H)-5-HETE together with an excess of unlabeled 5-HETE to each tube, the mixture is extracted with chloroform/methanol. The organic layer is washed with dilute acid and an aliquot is transferred to glass tubes and dried. The residue is dissolved in a small volume of chloroform and an aliquot is spotted on silica gel TLC sheets, which are developed with an ethyl acetate/isooctane/water acetic acid solvent system. The 5-HETE spots are visualized with iodine, cut out and placed in scintillation vials for counting. After adjusting the extraction efficiency, the amount (pmole) of [$^{14}$C]-5-HETE in each of the tubes is quantitated. The net pmoles of 5-HETE are obtained by substracting the pmoles of 5-HETE in the tubes containing buffer alone (blank) from the pmoles of 5-HETE in the tubes containing buffer and cells (control). The ability of the test compounds to modulate the activity of this enzyme is determined by a decrease or increase in the net amount of 5-HETE produced.

Table I shows the concentration required for inhibition of the 5-lipoxygenase (5-LOX/I$_{50}$ μm) for representative compounds according to the present invention.

TABLE I

| COMPOUND OF EXAMPLE | 5-LOX, Rat | I$_{50}$ (uM) Human | 12-LOX |
|---|---|---|---|
| 1 | .3 | .12 | I$_{42}$ = 30 |
| 2 | .3 | .35 | 1.5 |
| 3 | 1. | 2. | 5. |
| 5 | .6 | — | — |

What is claimed is:

1. A compound of the formula:

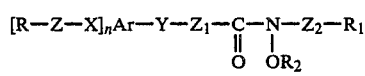

and pharmaceutically acceptable salts thereof wherein
Ar is phenyl;
Y is O or CR$_3$R$_4$;
X is O or CR$_3$R$_4$;
Z and Z$_1$ are independently a chemical bond or an alkylene chain having up to 6 carbon atoms in the principal chain and up to a total of 10 carbon atoms;
Z$_2$ is a chemical bond or an alkylene chain or a monosubstituted alkylene chain containing up to 6 carbon atoms in the principal chain and up to a total of 10 carbon atoms and the substituents are hydrogen, C$_1$-C$_5$ alkyl, C$_1$-C$_5$ alkoxy, or C$_1$-C$_5$ carbalkoxy;
R is quinolyl;
R$_1$ is hydrogen, C$_1$-C$_5$ alkyl, C$_3$-C$_5$ cycloalkyl, phenyl or quinolyl;
R$_2$, R$_3$ and R$_4$ are each hydrogen or C$_1$-C$_5$ alkyl;
and n is an integer from 0-2, with the proviso that when n=0,
R$_1$ is quinolyl.

2. The compound according to claim 1 wherein Y is O or CR$_3$R$_4$.

3. The compound according to claim 1 wherein X is O or CR$_3$R$_4$.

4. The compound according to claim 1 wherein Z and Z$_1$ are each a chemical bond or an alkylene chain containing up to 3 carbon atoms in the principal chain.

5. The compound according to claim 1 wherein Z$_2$ is an alkylene chain containing up to 5 carbon atoms in the principal chain.

6. A compound of the formula:

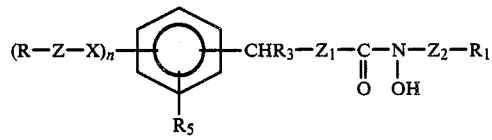

and pharmaceutically acceptable salts thereof; wherein
R is quinolyl;
R$_1$ is hydrogen, C$_1$-C$_5$ alkyl, or phenyl;
Z and Z$_1$ are independently a chemical bond or an alkylene chain having up to 6 carbon atoms in the principal chain and up to a total of 10 carbon atoms;
Z$_2$ is a chemical bond or an alkylene chain or a monosubstituted alkylene chain containing up to 6 carbon atoms in the principal chain and up to a total of 10 carbon atoms and the substituents are hydrogen, C$_1$-C$_5$ alkyl, or carboxy;
X is independently O or CR$_3$R$_4$;
R$_3$ is independently hydrogen or C$_1$-C$_5$ alkyl;
n is 0, 1 or 2; and
R$_5$ is hydrogen.

7. The compound according to claim 1 which is α-(3-(2-quinolylmethoxy)phenyl)-N-(2-phenethyl)-acetohydroxamate.

8. The compound according to claim 1 which is N-hydroxy-N-methyl-3-((2-quinolyl)methoxy)phenyl acetamide.

9. The compound according to claim 1 which is N-hydroxy-N-methyl-4-((2-quinolyl)methoxy)phenyl acetamide.

10. A compound having the formula:

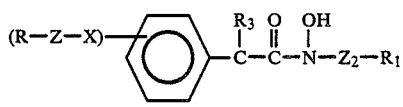

and pharmaceutically acceptable salts thereof, wherein
R is quinolyl;
Z is a chemical bond or C$_{1-3}$ alkylene;
X is O or CR$_3$R$_4$;
Z$_2$ is a chemical bond or C$_{1-3}$ alkylene;
R$_1$ is C$_{1-3}$ alkyl, phenyl, carboxy, or phenyl substituted with methoxy or chlorine;

each $R_3$ is independently hydrogen or $C_{1-3}$ alkyl; and $R_4$ is hydrogen or $C_{1-3}$ alkyl.

11. A therapeutic composition comprising a compound according to claim 1 and a pharmaceutical carrier therefor.

12. A method of treating hypersensitive disease, inflammatory conditions or allergic responses in a mammal comprising the administration to said mammal of a therapeutically effective amount of a compound according to claim 1.

* * * * *